United States Patent [19]

Shono et al.

[11] 4,384,144
[45] May 17, 1983

[54] PROCESS FOR PREPARING CYCLOPENTENONE DERIVATIVES

[75] Inventors: Tatsuya Shono, Kyoto; Yoshihiro Matsumura, Takatsuki, both of Japan

[73] Assignee: Otsuka Kagaku Yakuhin Kabushiki Kaisha, Osaka, Japan

[21] Appl. No.: 296,367

[22] Filed: Aug. 26, 1981

[63] Continuation-in-part of Ser. No. 778,452, Mar. 17, 1977, abandoned.

[30] Foreign Application Priority Data

Apr. 5, 1976 [JP] Japan .................................. 51/38405

[51] Int. Cl.³ .................... C07C 45/59; C07C 45/61
[52] U.S. Cl. .................... 568/347; 568/386; 560/231
[58] Field of Search ............... 568/386, 347; 560/231

[56] References Cited

U.S. PATENT DOCUMENTS 2,387,587 10/1945 Hunsdiecker ............... 260/588
2,661,374 12/1953 Schechter et al. ........... 568/347
2,768,965 10/1956 Stansbury et al. ........... 568/347
3,387,003 6/1968 Martel et al. ............... 568/347
3,591,643 7/1971 Fanta et al. ................. 568/347

FOREIGN PATENT DOCUMENTS 45-24771 8/1970 Japan .......................... 568/387
603422 10/1946 United Kingdom ......... 568/347

OTHER PUBLICATIONS

Kankaanpera, Chem. Abst., vol. 71, #12227h (1969).
Journal Organic Chemistry 35, 320 (1970).

Primary Examiner—James H. Reamer
Attorney, Agent, or Firm—Armstrong, Nikaido, Marmelstein & Kubovcik

[57] ABSTRACT

A process for preparing cyclopentenone derivatives represented by the formula:

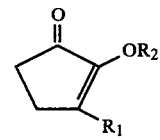

wherein $R_1$ is methyl or ethyl, and $R_2$ is hydrogen, methyl or acetyl, characterized in that a 1,4-diketone derivative represented by the formula:

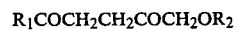

$R_1COCH_2CH_2COCH_2OR_2$ wherein $R_1$ and $R_2$ are as defined above is cyclized in the presence of a basic catalyst.

9 Claims, No Drawings

PROCESS FOR PREPARING CYCLOPENTENONE DERIVATIVES

This is a continuation-in-part of application Ser. No. 778,452, filed Mar. 17, 1977, now abandoned.

BACKGROUND OF THE INVENTION

This invention relates to a process for preparing cyclopentenone derivatives.

The compounds contemplated by the invention are cyclopentenone derivatives represented by the formula:

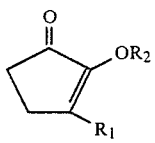
(1)

wherein $R_1$ is methyl or ethyl, and $R_2$ is hydrogen, methyl or acetyl. The cyclopentenone derivatives of this invention are known and are very useful in giving enhanced flavors to foods, beverages, livestock feed, etc.

The cyclopentenone derivatives are heretofore produced by various processes which generally require many and complex steps, give isomers that are difficult to separate, or necessitate the use of hazardous chemicals entailing environmental problems.

For example, J. Org. Chem. 35, 3203 (1970) discloses one of the processes. With this process, the reaction proceeds as follows:

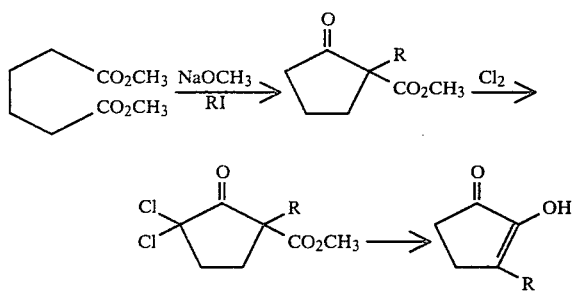

However, this process has various drawbacks, such as low yields (50 to 60%), the use of expensive starting materials and of hazardous and harmful chemicals such as metal sodium and similar highly basic substances, chlorine gas, etc.

An object of this invention is to provide a simplified process for preparing cyclopentenone derivatives.

Another object of this invention is to provide a process for preparing cyclopentenone derivatives in good yields.

Another object of this invention is to provide a process for preparing cyclopentenone derivatives without using hazardous chemicals and, therefore, free of environmental problems.

These and other objects of this invention will become apparent from the following description.

SUMMARY OF THE INVENTION

The present invention provides a process for preparing cyclopentenone derivatives represented by the formula:

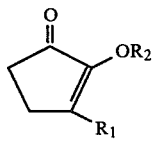
(1)

wherein $R_1$ is methyl or ethyl, and $R_2$ is hydrogen, methyl or acetyl by cyclizing a 1,4-diketone derivative represented by the formula:

$$R_1COCH_2CH_2COCH_2OR_2 \quad (2)$$

wherein $R_1$ and $R_2$ are as defined above, in the presence of a basic catalyst.

We have found that the cyclopentenone derivatives of the Formula (1), the desired products of this invention, can be prepared readily in high yields by contacting the 1,4-diketone derivative of the formula (2) with a basic catalyst. This invention is based on this novel finding.

According to this invention, the desired cyclopentenone derivatives are obtainable in high yields by a simplified process without giving isomers which are difficult to separate and without using hazardous chemicals which would lead to environmental pollution.

The 1,4-diketone derivative (2), the starting material of the invention, is novel and may be prepared, for example, by the processes shown below:

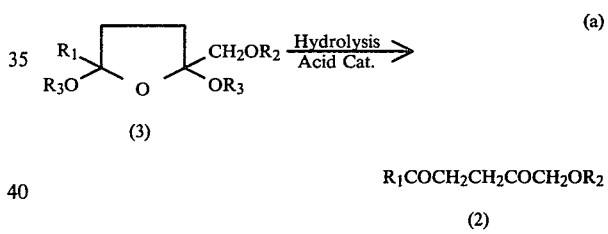

(a)

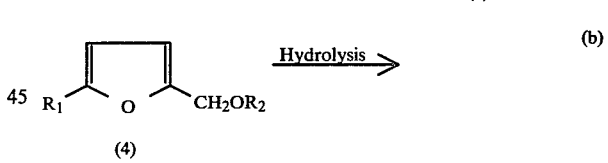

(b)

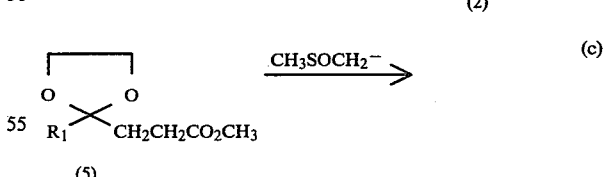

(c)

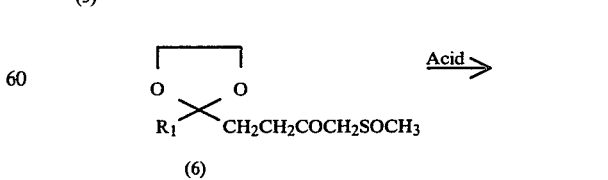

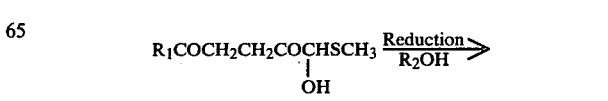

-continued $$R_1COCH_2CH_2COCH_2OR_2$$

(2)

In the processes (a) to (c) illustrated above, $R_1$ and $R_2$ are as defined above, and $R_3$ is methyl or ethyl.

In the process (a), the hydrolysis of a tetrahydrofuran derivative (3), a novel compound, in the presence of an acid catalyst readily affords the 1,4-diketone derivative (2). In fact, we have found for the first time that the novel compound (3) yields the 1,4-diketone derivative (2), the starting material of this invention, and that the compound (3) gives the desired compound (1) of the invention in high yields by way of intermediate (2).

Processes (b) and (c) are also believed to be suitable for preparing the 1,4-diketone derivative (2). With the process (b), the 2,5-di-substituted furan derivative (4), when hydrolyzed, affords the compound (2). According to the process (c), a γ-keto-acid ester (5) wherein the carbonyl group is protected in the form of a ketal is reacted with dimsyl anion ($CH_3SOCH_2^-$) to obtain a sulfoxide derivative (6), which is then treated with an acid and is thereafter reduced and alkylated, giving the compound (2).

As illustrated below, the novel tetrahydrofuran derivative (3) can be easily prepared, for example, by electrolytically oxidizing a 5-alkyl-2-furfuryl alcohol derivative (7) to obtain a 2,5-dihydrofuran derivative (8) and reducing the derivative (8).

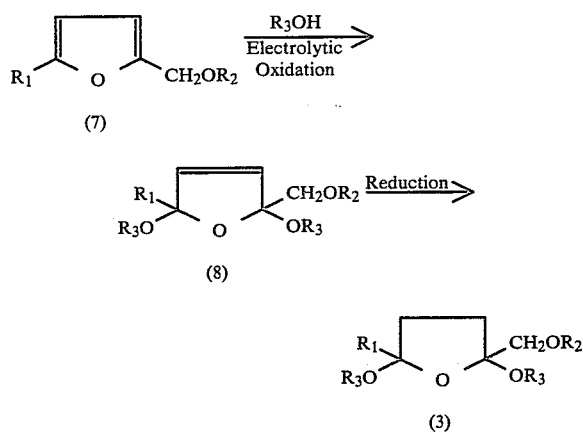

In the above equation, $R_1$, $R_2$ and $R_3$ are as defined above. Typical of such tetrahydrofuran derivatives (3) are 2,5-dimethoxy-5-methyltetrahydrofurfuryl alcohol, 2,5-dimethoxy-5-ethyltetrahydrofurfuryl alcohol, 2,5-diethoxy-5-methyltetrahydrofurfuryl alcohol, the methyl ether of 2,5-dimethoxy-5-methyltetrahydrofurfuryl alcohol, the acetate of 2,5-dimethoxy-5-methyltetrahydrofurfuryl alcohol, and the like.

Representative of useful 1,4-diketone derivatives (2) are 2,5-diketohexanol-1, 2,5-diketoheptanol-1, 2,5-diketohexyl methyl ester, 2,5-diketoheptyl methyl ether, 2,5-diketohexyl acetate, 2,5-diketoheptyl acetate, and the like.

As already stated, the desired compounds (1) of this invention are prepared by subjecting the 1,4-diketone derivative to cyclization in the presence of a basic catalyst. Generally, it is preferably to effect this reaction with the use of a solvent. The preferred solvents are those which will not interfere with the reaction, such as water, methanol, ethanol and like alcohols; diethyl ether, tetrahydrofuran, dimethoxyethane, dioxane and like ethers; methylene chloride, chloroform and like hydrocarbon halides; dimethylformamide, dimethylsulfoxide, hexamethylphosphorylamide and like non-protonic polar solvents; and the like. Examples of useful basic catalysts are hydroxides, carbonates, bicarbonates and acetates of alkali metals and alkaline earth metals; trimethylamine, triethylamine, pyridine and like amines; basic ion exchange resins, and the like. Preferred are carbonates of alkali metals and alkaline earth metals, triethylamine and basic ion exchange resins. The catalyst is useable in widely varying amounts. Usually it is desirable to use, per mol of the 1,4-diketone derivative (2), about 500 to about 2000 ml, preferably about 800 to 1200 ml, of a solution containing about 0.5 to about 5 wt./vol. % of the catalyst. The reaction temperature and the reaction pressure may be suitably determined. Preferably the reaction is conducted at room temperature to about 130° C. at atmospheric pressure.

As previously described, the desired compounds (1) of this invention can be prepared also by hydrolyzing the tetrahydrofuran derivative (3) in the presence of an acid catalyst to obtain the 1,4-diketone derivative (2) as an intermediate and cyclizing the intermediate in the presence of a basic catalyst. It is one of our novel findings that the hydrolysis of the tetrahydrofuran derivative (3) gives the 1,4-diketone derivative (2). With this process, the 1,4-diketone derivative (2) obtained by the ring cleavage of the tetrahydrofuran derivative (3) may be cyclized after having been isolated from the resulting reaction mixture or without being isolated therefrom.

The acid catalysts useful for the hydrolysis include, for example, inorganic acids such as hydrochloric acid, sulfuric acid, phosphoric acid and perchloric acid; organic acids such as formic acid, acetic acid and propionic acid; sulfonic acids such as methanesulfonic acid, benzenesulfonic acid and p-toluenesulfonic acid; Lewis acids such as boron trifluoride, aluminum chloride, zinc chloride and titanium tetrachloride; acid ion exchange resins, and the like. Preferred are hydrochloric acid, sulfuric acid, perchloric acid and acid ion exchange resins. Although such catalyst is usable in widely varying amounts, it is usually advantageous to use, per mol of the tetrahydrofuran derivative (3), about 300 to about 1500 ml, preferably about 500 to about 700 ml, of a solution containing about 0.1 to about 5 wt./vol.% of the catalyst. Generally the hydrolysis is conducted in water or in an aqueous medium such as water-ethanol, the water being employed in at least the theoretical amount for the hydrolysis. The reaction, which will proceed fully at low temperatures, is conducted preferably at an elevated temperature of about $-15°$ to about 100° C. The hydrolysis reaction gives the 1,4-diketone derivative (2) in high yields.

The resulting 1,4-diketone derivative (2) can be cyclized in the same manner as previously described to obtain the desired compound (1) of this invention.

The cyclopentenone derivatives (1) prepared by the process of this invention can be purified easily by a known method, for example by filtering, extracting or distilling the reaction product. Because the present process yields the desired product without involving the formation of complicated isomers, the reaction product can be purified with extreme ease.

Typical examples of the compounds (1) obtained by the present process are 2-hydroxy-3-methylcyclopentenone; 2-hydroxy-3-ethylcyclopentenone; 2-methoxy-3- methyl-cyclopentenone; 2-methoxy-3-ethylcyclopentenone; 2-acetoxy-3-methylcyclopentenone; 2-acetoxy-3-ethylcyclopentenone; and the like.

Examples of this invention will be given below in which the precentage indicating the concentration of catalyst solution is wt.%vol.%.

EXAMPLE 1

30 ml quantity of distilled water and 1 g (wet weight) of strong acid ion exchange resin are added to 8.8 g (0.05 mol) of 2,5-dimethoxy-5-methyltetrahydrofurfuryl alcohol. The mixture is stirred at room temperature for 15 minutes, extracted with methylene chloride three times and dried. Removal of the solvent from the dried mixture by distillation gives an oily product. To the oily product is immediately added 100 ml of 1% aqueous solution of sodium carbonate and the mixture is refluxed with heating for 3 hours. The reaction mixture is cooled, then extracted with chloroform five times, and the combined chloroform solution is dried over anhydrous magnesium sulfate. The dried product is separated from the drying agent and distilled to remove the solvent, affording 2-hydroxy-3-methylcyclopentenone, the desired product, in the form of crystals in a yield of 80% based on 2,5dimethoxy-5-methyltetrahydrofurfuryl alcohol, m.p. 105°–106° C.

Further, another oily product is prepared in the same manner as above and distilled at reduced pressure to give 2,5-diketohexanol-1 in a yield of 90%, b.p. 80°–83° C./0.2 mm Hg and m.p. 25°–26° C.

EXAMPLE 2

A mixture of 13 g (0.1 mol) of 2,5-diketo-hexanol-1 and 100 ml of 1% aqueous solution of potassium carbonate is refluxed with heating for 3 hours and then cooled. The reaction mixture is extracted with chloroform three times, and the combined chloroform solution is treated in the same manner as in Example 1, giving 2-hydroxy-3-methylcyclopentenone, the desired product, in the form of crystals in a yield of 90%, m.p. 105°–106° C.

EXAMPLE 3

A mixture of 14.4 g (0.1 mol) of 2,5-diketo-heptanol-1 and 100 ml of 1% methanol solution of sodium hydroxide is refluxed with heating for 3 hours and then cooled. The reaction mixture is thereafter carefully neutralized with acetic acid and subsequently distilled at room temperature and at reduced pressure to remove the methanol. The resulting residue is extracted with ethyl acetate. 2-hydroxy-3-ethylcyclopentenone, the desired product, can be readily obtained by distilling off the ethyl acetate from the extract at reduced pressure, yield 92% and m.p. 40°–42° C.

EXAMPLE 4

A 3.06 g quantity (0.0212 mol) of methyl ether of 2,5-diketohexanol-1 is added to 15 ml of dioxane containing 5% of triethylamine, and the mixture is heated at 100° C. for 2 hours. The reaction product is carefully neutralized with acetic acid and thereafter distilled at reduced pressure, giving 2-methoxy-3-methylcyclopentenone, the desired product, in a yield of 88%, b.p. 84°–85° C./18 mm Hg.

EXAMPLE 5

A 17.2 g quantity (0.1 mol) of acetate of 2,5-diketohexanol-1 is dissolved in 100 ml of dimethylformamide, 2 g (wet weight of basic ion exchange resin is added to the solution and the mixture is heated at 130° C. for 3 hours. The ion exchange resin is filtered off from the reaction mixture. Distillation of the filtrate gives 2-acetoxy-3-methylcyclopentenone, the desired product, in a yield of 75%, b.p. 120°–122° C./13 mm Hg.

What is claimed is:

1. A process for preparing a cyclopentenone derivative of the formula:

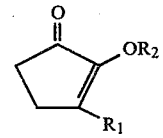

wherein $R_1$ is methyl or ethyl, and $R_2$ is hydrogen, methyl or acetyl, comprising cyclizing a 1,4-diketone derivative of the formula:

wherein $R_1$ and $R_2$ are as defined above, at a temperature of from room temperature to about 130° C. in the presence of a basic catalyst selected from the group consisting of hydroxides, carbonates, bicarbonates and acetates of alkali metals and of alkaline earth metals; trimethylamine; triethylamine; pyridine and basic ion exchange resins.

2. A process for preparing cyclopentenone derivatives of the formula:

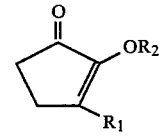

wherein $R_1$ is methyl or ethyl, and $R_2$ is hydrogen, methyl or acetyl, comprising: hydrolyzing a tetrahydrofuran derivative of the formula:

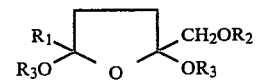

wherein $R_1$ and $R_2$ are as defined above, and $R_3$ is methyl or ethyl, at a temperature of from about −15° to about 100° C. and in the presence of an acid catalyst to produce a 1,4-diketone derivative represented by the formula:

wherein $R_1$ and $R_2$ are as defined above; and cyclizing the 1,4-diketone derivative at a temperature of from room temperature to about 130° C. in the presence of a basic catalyst selected from the group consisting of hydroxides, carbonates, bicarbonates and acetates of alkali metals and of alkaline earth metals; trimethylamine; triethylamine; pyridine and basic ion exchange resins.

3. A process as defined in claim 1 wherein the basic catalyst is a member selected from the group consisting of carbonates of alkali metals and alkaline earth metals; triethylamine and basic ion exchange resins.

4. A process as defined in claim 2 wherein the 1,4-diketone derivative is subjected to cyclization without being separated from the hydrolysis reaction mixture of the tetrahydrofuran derivative.

5. A process as defined in claim 2 wherein the acid catalyst is a member selected from the group consisting of hydrochloric acid, sulfuric acid, phosphoric acid, perchloric acid, formic acid, acetic acid, propionic acid, methanesulfonic acid, benzenesulfonic acid, p-toluenesulfonic acid, boron trifluoride, aluminum chloride, zinc chloride, titanium tetrachloride and acid ion exchange resins.

6. A process as defined in claim 5 wherein the acid catalyst is a member selected from the group consisting of hydrochloric acid, sulfuric acid, perchloric acid and acid ion exchange resins.

7. A process as defined in claim 2 wherein the basic catalyst is a member selected from the group consisting of carbonates of alkali metals and of alkaline earth metals; triethylamine and basic ion exchange resins.

8. A process for preparing a cyclopentenone derivative as in claim 1 wherein $R_2$ is hydrogen.

9. A process for preparing a cyclopentenone derivative as in claim 2 wherein $R_2$ is hydrogen.

* * * * *